US010539482B2

(12) United States Patent
McQuillen et al.

(10) Patent No.: US 10,539,482 B2
(45) Date of Patent: Jan. 21, 2020

(54) OXYGEN SENSOR ELEMENT BLACKENING DETECTION

(71) Applicant: Ford Global Technologies, LLC, Dearborn, MI (US)

(72) Inventors: Michael McQuillen, Warren, MI (US); Gopichandra Surnilla, West Bloomfield, MI (US); Richard E. Soltis, Saline, MI (US); Daniel A. Makled, Dearborn, MI (US); John Joseph Virga, Farmington Hills, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 22 days.

(21) Appl. No.: 16/022,034

(22) Filed: Jun. 28, 2018

(65) Prior Publication Data
US 2018/0306673 A1    Oct. 25, 2018

Related U.S. Application Data

(62) Division of application No. 15/002,199, filed on Jan. 20, 2016, now Pat. No. 10,078,033.

(51) Int. Cl.
  *G01M 15/10* (2006.01)
  *G01N 27/417* (2006.01)
(52) U.S. Cl.
  CPC ...... *G01M 15/104* (2013.01); *G01N 27/4175* (2013.01)
(58) Field of Classification Search
  CPC .......................... G01M 15/102; G01M 15/104

USPC ............... 73/114.69, 114.71, 114.73
See application file for complete search history.

(56) References Cited

U.S. PATENT DOCUMENTS

| | | | |
|---|---|---|---|
| 4,860,712 A | 8/1989 | Nakajima et al. | |
| 5,781,878 A | 7/1998 | Mizoguchi et al. | |
| 6,266,993 B1 | 7/2001 | Diehl et al. | |
| 6,360,583 B1* | 3/2002 | Soltis | F02D 41/1495 73/23.31 |
| 9,856,799 B1* | 1/2018 | McQuillen | F02D 41/1456 |
| 9,857,330 B2 | 1/2018 | Ledermann | |
| 2002/0139670 A1* | 10/2002 | Beckmeyer | G01N 27/4071 204/429 |
| 2004/0055886 A1 | 3/2004 | Gruenwald | |
| 2005/0043899 A1 | 2/2005 | Strassner et al. | |
| 2005/0252771 A1 | 11/2005 | Wiedenmann et al. | |
| 2007/0010932 A1* | 1/2007 | Gotoh | F01N 11/00 701/114 |
| 2009/0308135 A1 | 12/2009 | Reinshagen et al. | |
| 2011/0139618 A1* | 6/2011 | Serrels | G01N 27/4071 204/408 |
| 2012/0001641 A1 | 1/2012 | Tsukada et al. | |
| 2012/0167650 A1 | 7/2012 | Webb et al. | |

(Continued)

*Primary Examiner* — Eric S. McCall
(74) *Attorney, Agent, or Firm* — Geoffrey Brumbaugh; McCoy Russell LLP

(57) ABSTRACT

The present description relates generally to methods and systems for detecting thermal aging and blackening in oxygen sensors. Thermal aging and blackening effects may be differentiated based on a monitored change in impedance in each of a pump cell and a Nernst cell of the oxygen sensor following application of an alternating voltage. In response to detection of thermal aging and/or blackening in the oxygen sensor corrective measures may be taken to ensure accurate oxygen estimation using the sensor.

4 Claims, 6 Drawing Sheets

(56) References Cited

U.S. PATENT DOCUMENTS

| | | |
|---|---|---|
| 2012/0167656 A1 | 7/2012 | Verdier et al. |
| 2014/0076741 A1 | 3/2014 | Adams |
| 2015/0253282 A1* | 9/2015 | Satou ................. G01N 27/4071 204/429 |
| 2016/0103095 A1* | 4/2016 | Surnilla ................. G01N 27/41 205/784.5 |
| 2016/0109422 A1* | 4/2016 | Makled ............. G01N 33/0073 73/23.32 |
| 2016/0169138 A1* | 6/2016 | McQuillen .......... F02D 41/1494 219/497 |
| 2017/0097318 A1 | 4/2017 | Adams |

* cited by examiner

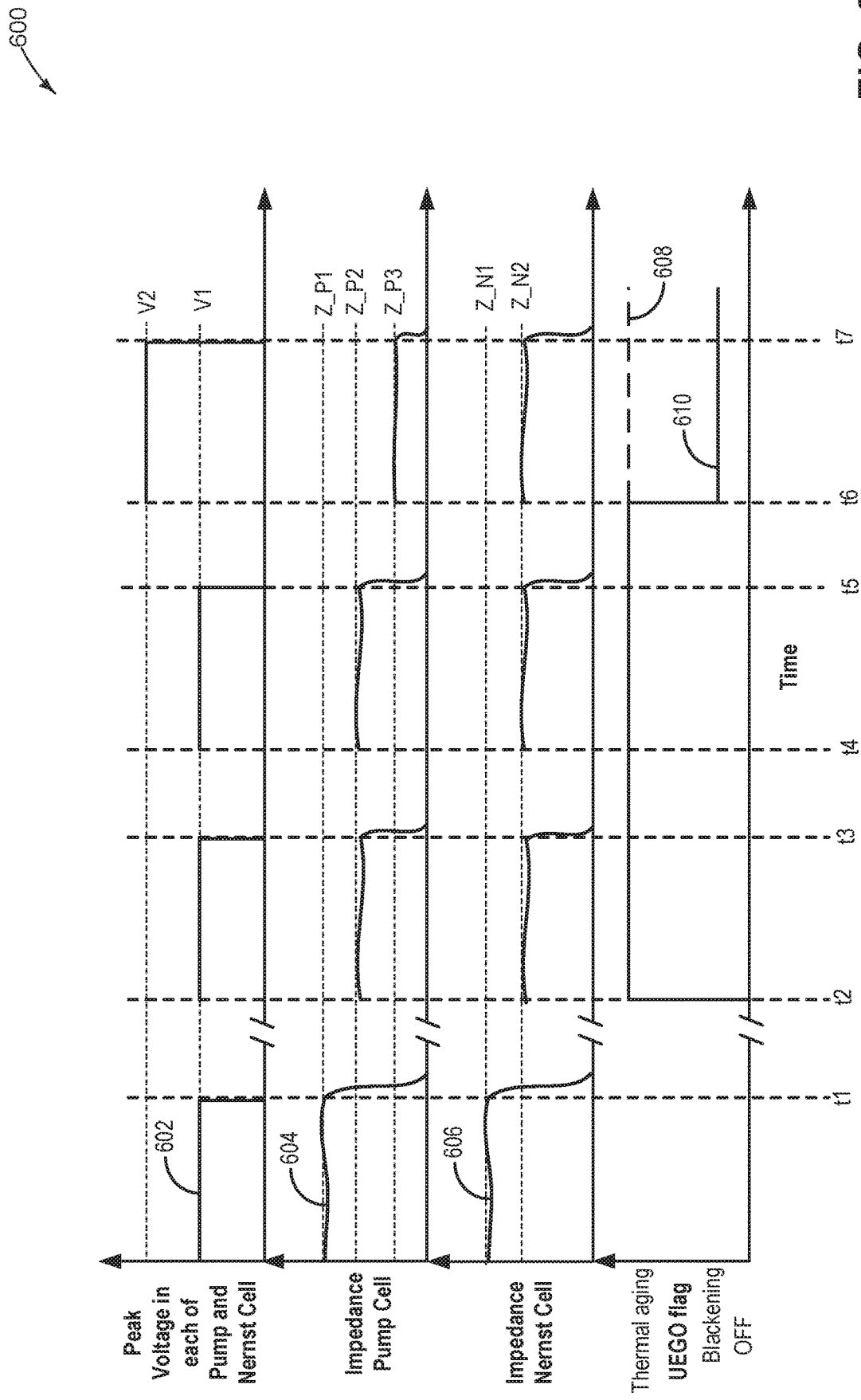

OXYGEN SENSOR ELEMENT BLACKENING DETECTION

CROSS REFERENCE TO RELATED APPLICATION

The present application is a divisional of U.S. patent application Ser. No. 15/002,199, entitled "OXYGEN SENSOR ELEMENT BLACKENING DETECTION," filed on Jan. 20, 2016. The entire contents of the above-referenced application are hereby incorporated by reference in its entirety for all purposes.

FIELD

The present description relates generally to methods and systems for detecting thermal aging and/or blackening in oxygen sensors.

BACKGROUND/SUMMARY

Intake and/or exhaust gas sensors may be operated to provide indications of various intake and exhaust gas constituents. Output from a Universal Exhaust Gas Oxygen (UEGO) sensor, for example, may be used to determine the air-fuel ratio (AFR) of exhaust gas. Similarly, an oxygen sensor may be disposed in an engine intake passage to determine the humidity of intake gas or the composition of exhaust gases being recirculated to the intake. Indications of intake and exhaust gas oxygen content may be used to adjust various engine operating parameters, such as fueling. As an example, cylinder fueling may be feedback controlled based on exhaust gas AFR to achieve a target combustion AFR that maximizes the operating efficiency of an exhaust emission control device. As such, the measurement accuracy of an oxygen sensor may be significantly affected by degradation of an element in the oxygen sensor, such as due to sensor element blackening or thermal aging. Oxygen sensor element blackening is a form of degradation which may occur due to application of high and/or variable voltage and due to low oxygen and water conditions. Thermal aging is another form of degradation that occurs due to continuous operation of the sensor over a period of time.

Various approaches have been used to detect oxygen sensor degradation especially in relation to blackening and thermal aging. In one example approach, shown by Verdier et al. in US 20120167656 A1, a voltage may be applied to terminals connected to electrodes of a pump cell (in the case of a dual-cell) sensor or that of a combined pump and measuring cell (in the case of a single-cell sensor) of the exhaust gas sensor and a pumping current flowing through the cell is subsequently monitored. Voltages of equal magnitudes may be applied to the terminals at different points of time and the difference in pumping current is estimated. If the difference in pumping current is higher than a threshold value, oxygen sensor degradation due to blackening of at least one of the cell electrodes may be inferred.

The inventors herein have recognized potential issues with the above mentioned approach. As one example, following an application of voltage at two different points of time, a change in pumping current may occur due to thermal aging or element blackening. Consequently, in the approach of Verdier et al., it may not possible to differentiate between thermal aging of the sensor and sensor element blackening. Based on the occurrence of thermal aging and/or element blackening, different corrective measures for future oxygen estimations using the sensor are required to be taken. By applying inappropriate corrective measures to UEGO sensors, sensor degradation may be accelerated and the accuracy of oxygen estimation using the sensor may decrease thereby affecting engine performance.

The inventors herein have identified an approach by which the issue described above may be at least partly addressed. One example method for a vehicle engine comprises differentiating between thermal aging and blackening of an oxygen sensor element based on a monitored change in impedance of each of a pump cell and a Nernst cell of the oxygen sensor following application of a voltage. In this way, oxygen sensor blackening can be identified more reliably and promptly addressed.

As an example, impedance of each of a pump and a Nernst cell of an oxygen sensor may be monitored and used for detection and differentiation of sensor thermal aging and sensor element blackening. Thermal aging (also termed as de-graining effect) may occur in the oxygen sensor after multiple usages over time. Blackening may occur due to change in the material (e.g., Zirconia ($ZrO_2$) into Zirconium (Zr)) present in the electrodes of the pump cell. A dark accumulation (e.g., of metallic Zr) may be observed on an electrode of the sensor, which may be termed as blackening. An alternating current (AC) voltage may be opportunistically or periodically applied to each of the pump cell and the Nernst cell of the oxygen sensor and the corresponding impedance of the cells may be estimated by measuring the respective pumping currents to generate a frequency scan. The impedance of each of the pump cell and Nernst cell may reduce due to heating over time. Thermal aging may be detected based on the change in impedance over time. However, after a period of time and after multiple usages, the change in impedance (observed in both pump and Nernst cell) due to thermal aging may stabilize. Further application of voltage to each of the cells may not show any further reduction in impedance. If there is blackening present in an electrode of the pump cell, after stabilization of thermal aging, further application of an AC voltage of higher peak voltage value may show a significant change in pump cell impedance. The extent of blackening may be estimated from the amount of change observed in the pump cell impedance relative to a previous measurement of pump cell impedance (such as during a last scan). Also, upon application of the same AC voltage to the Nernst cell, there may not be any further change in impedance, further confirming that a change in resistance observed in the pump cell is due to blackening and not from any further thermal aging. Following the detection of thermal aging, a compensation factor used during oxygen estimation using the sensor may be updated. In comparison, upon detection of sensor blackening, a lower target (reference) voltage and a conservative ramp rate for reference voltage application may be used during future oxygen estimation. Further, a diagnostic code (flag) may be set to notify the user of the degradation.

In this way, a change in impedance (or resistance) in each of the pump and the Nernst cell over time may be used to differentiate between thermal aging effects and element blackening in an oxygen sensor. By actively monitoring impedances of each of the pump and the Nernst cell following an application of alternating voltage, over time, it is possible to detect element blackening with higher certainty and better differentiate between the two forms of UEGO sensor degradation. The technical effect of differentiating between thermal aging effects and element blackening in an oxygen sensor is that appropriate corrective measures may be employed accordingly. By updating a corrective factor to compensate for thermal aging effects, accuracy of oxygen estimation may be maintained as a sensor ages. In comparison, when element blackening is detected, further damage to the sensor due to blackening may be limited by taking preventive measures such as applying a lower target voltage and a conservative ramp rate of reference voltage during oxygen estimations. Overall, by effective detection and differentiation of thermal aging and element blackening, accuracy and reliability of oxygen sensor operation is increased, enabling engine performance to be maintained.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 6 shows an example of detecting thermal aging and blackening in an UEGO sensor based on change in pump and Nernst cell impedance.

DETAILED DESCRIPTION

Figure 4:
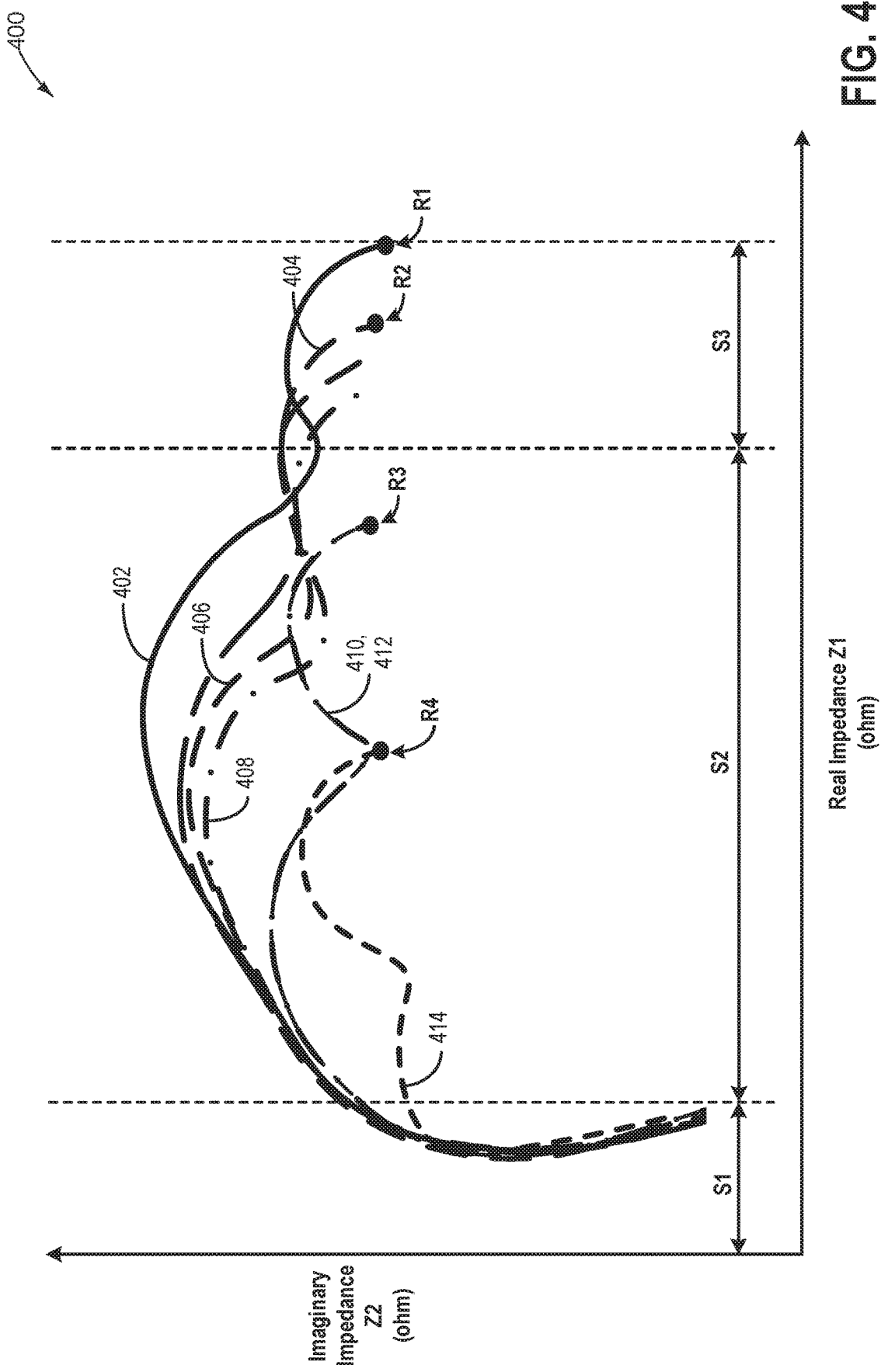
FIG. 4 shows an example plot of variation in Pump cell impedance over time for a plurality of frequency scans.
Figure 5:
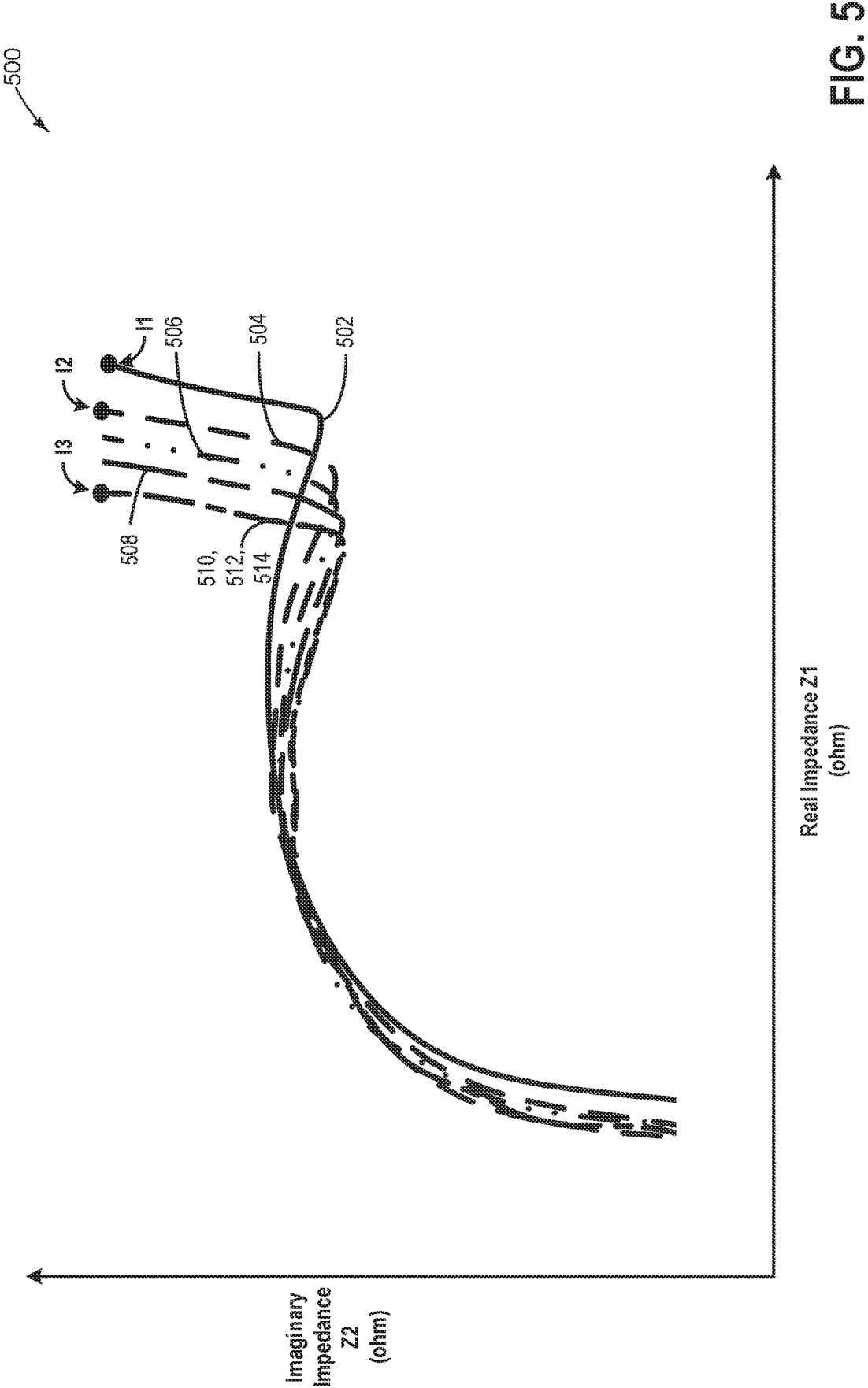
FIG. 5 shows an example plot of variation in Nernst cell impedance over time for a plurality of frequency scans.

The following description relates to systems and methods for thermal aging and blackening detection in oxygen sensors. Oxygen sensors may be disposed in an intake air passage or an exhaust gas passage, as shown in the engine system of FIG. 1. FIG. 2 shows a schematic view of an oxygen sensor that may be affected by thermal aging and/or blackening. An engine controller may be configured to perform a control routine, such as the example routine of FIG. 3, to detect thermal aging and element blackening in an oxygen sensor. FIGS. 4 and 5 show variation in Pump cell and Nernst cell impedance (over time) respectively, for a plurality of frequency scans. An example of detection of thermal aging and element blackening, based on change in pump and Nernst cell impedance, is shown in FIG. 6.

Figure 1:
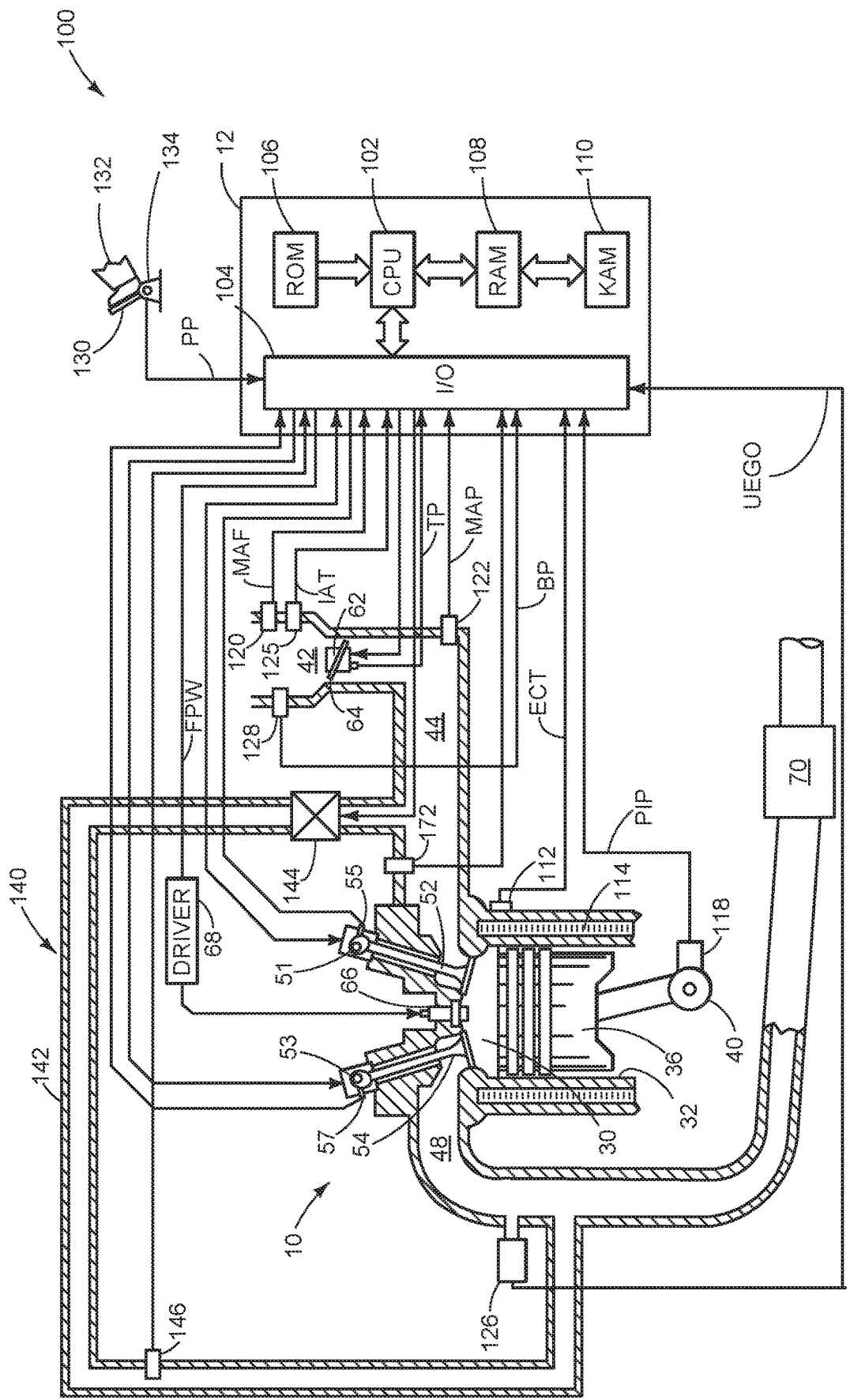
FIG. 1 shows an example engine system including intake and exhaust oxygen sensors.
Figure 2:
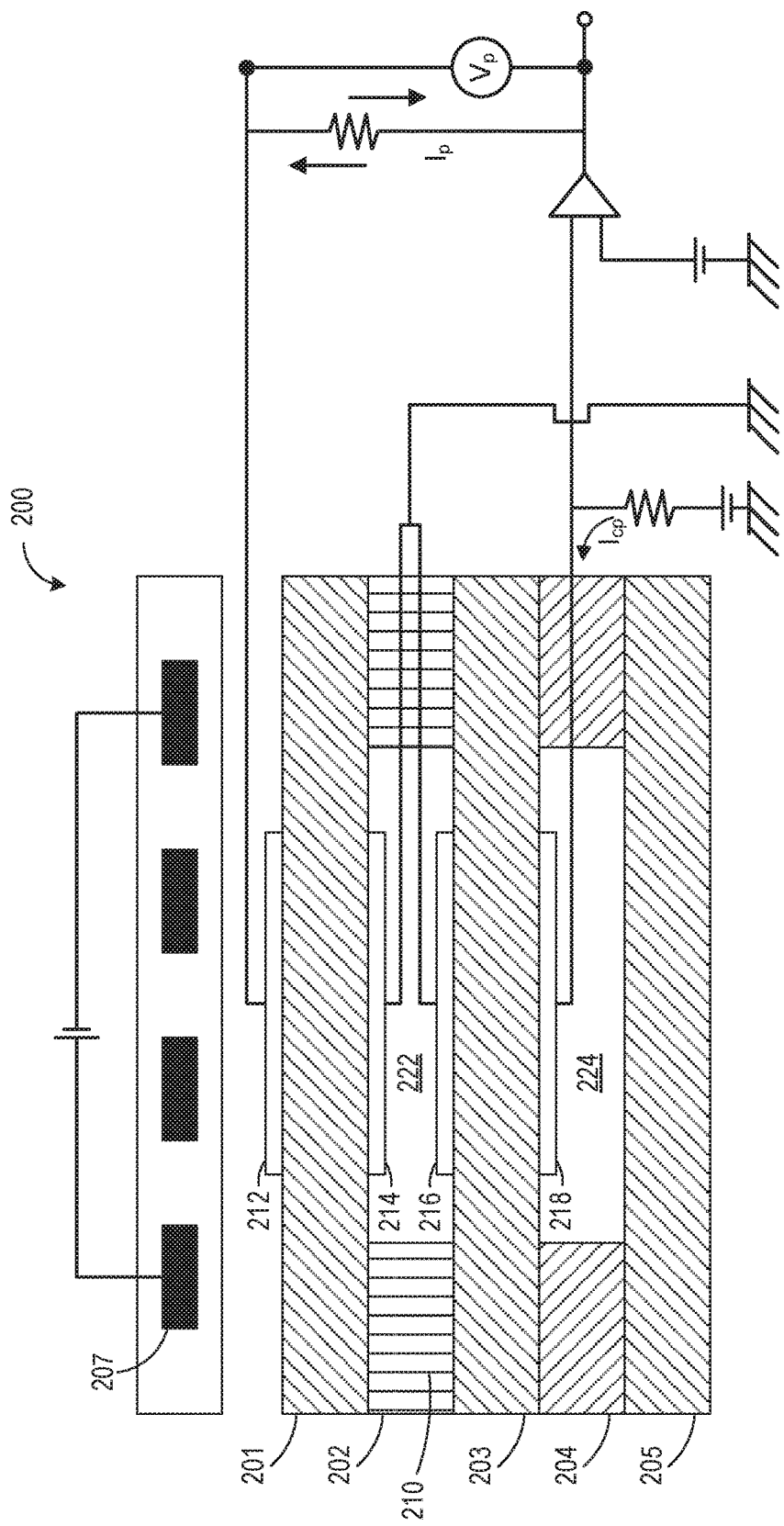
FIG. 2 shows a schematic diagram of an example UEGO sensor.

FIG. 1 is a schematic diagram showing one cylinder of a multi-cylinder engine 10 in an engine system 100. The engine 10 may be controlled at least partially by a control system including a controller 12 and by input from a vehicle operator 132 via an input device 130. In this example, the input device 130 includes an accelerator pedal and a pedal position sensor 134 for generating a proportional pedal position signal PP. A combustion chamber (cylinder) 30 of the engine 10 may include combustion chamber walls 32 with a piston 36 positioned therein. The piston 36 may be coupled to a crankshaft 40 so that reciprocating motion of the piston is translated into rotational motion of the crankshaft. The crankshaft 40 may be coupled to at least one drive wheel of a vehicle via an intermediate transmission system. Further, a starter motor may be coupled to the crankshaft 40 via a flywheel to enable a starting operation of the engine 10.

The combustion chamber 30 may receive intake air from an intake manifold 44 via an intake passage 42 and may exhaust combustion gases via an exhaust passage 48. The intake manifold 44 and the exhaust passage 48 can selectively communicate with the combustion chamber 30 via respective intake valve 52 and exhaust valve 54. In some embodiments, the combustion chamber 30 may include two or more intake valves and/or two or more exhaust valves.

In this example, the intake valve 52 and exhaust valve 54 may be controlled by cam actuation via respective cam actuation systems 51 and 53. The cam actuation systems 51 and 53 may each include one or more cams and may utilize one or more of cam profile switching (CPS), variable cam timing (VCT), variable valve timing (VVT), and/or variable valve lift (VVL) systems that may be operated by the controller 12 to vary valve operation. The position of the intake valve 52 and exhaust valve 54 may be determined by position sensors 55 and 57, respectively. In alternative embodiments, the intake valve 52 and/or exhaust valve 54 may be controlled by electric valve actuation. For example, the combustion chamber 30 may alternatively include an intake valve controlled via electric valve actuation and an exhaust valve controlled via cam actuation including CPS and/or VCT systems.

A fuel injector 66 is shown coupled directly to combustion chamber 30 for injecting fuel directly therein in proportion to the pulse width of signal FPW received from the controller 12 via an electronic driver 68. In this manner, the fuel injector 66 provides what is known as direct injection of fuel into the combustion chamber 30. The fuel injector may be mounted in the side of the combustion chamber or in the top of the combustion chamber (as shown), for example. Fuel may be delivered to the fuel injector 66 by a fuel system (not shown) including a fuel tank, a fuel pump, and a fuel rail. In some embodiments, the combustion chamber 30 may alternatively or additionally include a fuel injector arranged in the intake manifold 44 in a configuration that provides what is known as port injection of fuel into the intake port upstream of the combustion chamber 30.

The intake passage 42 may include a throttle 62 having a throttle plate 64. In this particular example, the position of throttle plate 64 may be varied by the controller 12 via a signal provided to an electric motor or actuator included with the throttle 62, a configuration that is commonly referred to as electronic throttle control (ETC). In this manner, the throttle 62 may be operated to vary the intake air provided to the combustion chamber 30 among other engine cylinders. The position of the throttle plate 64 may be provided to the controller 12 by a throttle position signal TP. The air intake passage 42 may include the intake air temperature (IAT) sensor 125 and the barometric pressure (BP) sensor 128. The IAT sensor 125 estimates intake air temperature to be used in engine operations and provides a signal to the controller 12. Similarly, the BP sensor 128 estimates the ambient pressure for engine operations and provides a signal to the controller 12. The intake passage 42 may further include a mass air flow sensor 120 and a manifold air pressure sensor 122 for providing respective signals MAF and MAP to the controller 12.

An exhaust gas sensor 126 is shown coupled to the exhaust passage 48 upstream of an emission control device 70. The sensor 126 may be any suitable sensor for providing an indication of exhaust gas air/fuel ratio (AFR) such as a linear oxygen sensor or UEGO (universal or wide-range exhaust gas oxygen), a two-state oxygen sensor or EGO, a HEGO (heated EGO), a NOx, HC, or CO sensor. In a first mode of operation of the oxygen sensor, exhaust gas my flow from a combustion engine into a first cavity formed on one side by a zirconium oxide layer and on another side by a ceramic layer, the ceramic layer positioned between the first cavity and a second cavity containing a reference gas. A first voltage may be applied across the zirconium oxide layer to pump oxygen ions between the first cavity and the exhaust gas and a second voltage may be applied across the ceramic layer and the first voltage may be limited when the second voltage reaches a threshold. Whereas in a second mode of operation of the oxygen sensor, breakdown of a portion of the zirconium oxide layer to zirconium may be detected by comparing a change in impedance of the zirconium layer to a change in impedance of the ceramic layer. A detailed embodiment of the UEGO sensor is described with reference to FIG. 2. An oxygen sensor may be used to estimate the AFR for both intake and exhaust gas. Based on AFR estimation, engine operating parameters e.g. fueling may be regulated. In addition, by utilizing AFR estimate in exhaust gas, operating efficiency of an emission control device may be improved. In order to improve engine operation it is important to be able to detect any degradation in the oxygen sensor(s). A detailed method for detection of oxygen sensor degradation due to each of thermal aging and element blackening will be discussed with reference to FIGS. 3-6.

The emission control device 70 is shown arranged along the exhaust passage 48 downstream of the exhaust gas sensor 126. The device 70 may be a three way catalyst (TWC), NOx trap, various other emission control devices, or combinations thereof. In some embodiments, during operation of the engine 10, the emission control device 70 may be periodically reset by operating at least one cylinder of the engine within a particular air/fuel ratio.

Further, an exhaust gas recirculation (EGR) system 140 may route a desired portion of exhaust gas from the exhaust passage 48 to the intake manifold 44 via an EGR passage 142. The amount of EGR provided to the intake manifold 44 may be varied by the controller 12 via an EGR valve 144. Further, an EGR sensor 146 may be arranged within the EGR passage 142 and may provide an indication of one or more of pressure, temperature, and constituent concentration of the exhaust gas. A linear oxygen sensor 172 may be positioned at the intake passage, downstream of the intake throttle, to facilitate EGR regulation. Under some conditions, the EGR system 140 may be used to regulate the temperature of the air and fuel mixture within the combustion chamber, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

The controller 12 is shown in FIG. 1 as a microcomputer, including a microprocessor unit 102, input/output ports 104, an electronic storage medium for executable programs and calibration values shown as read only memory chip 106 in this particular example, random access memory 108, keep alive memory 110, and a data bus. The controller 12 may receive various signals from sensors coupled to the engine 10, in addition to those signals previously discussed, including measurement of inducted mass air flow (MAF) from the mass air flow sensor 120; engine coolant temperature (ECT) from a temperature sensor 112 coupled to a cooling sleeve 114; a profile ignition pickup signal (PIP) from a Hall effect sensor 118 (or other type) coupled to crankshaft 40; throttle position (TP) from a throttle position sensor; and absolute manifold pressure signal, MAP, from the sensor 122. Engine speed signal, RPM, may be generated by the controller 12 from signal PIP. Manifold pressure signal MAP from a manifold pressure sensor may be used to provide an indication of vacuum, or pressure, in the intake manifold. Note that various combinations of the above sensors may be used, such as a MAF sensor without a MAP sensor, or vice versa. During stoichiometric operation, the MAP sensor can give an indication of engine torque. Further, this sensor, along with the detected engine speed, can provide an estimate of charge (including air) inducted into the cylinder. In one example, the sensor 118, which is also used as an engine speed sensor, may produce a predetermined number of equally spaced pulses every revolution of the crankshaft.

The storage medium read-only memory 106 can be programmed with computer readable data representing non-transitory instructions executable by the processor 102 for performing the methods described below as well as other variants that are anticipated but not specifically listed. As described above, FIG. 1 shows one cylinder of a multi-cylinder engine, and each cylinder may similarly include its own set of intake/exhaust valves, fuel injector, spark plug, etc.

The controller 12 receives signals from the various sensors of FIG. 1 and employs the various actuators of FIG. 1 to adjust engine operation based on the received signals and instructions stored on a memory of the controller 12. In one example, the controller 12 initiates a diagnostic routine to detect thermal aging and/or present in oxygen sensors 126 and 172.

FIG. 2 shows a schematic view of an example embodiment of an exhaust gas oxygen sensor, such as UEGO sensor 200, configured to measure a concentration of oxygen ($O_2$) in an exhaust gas stream during fueling conditions. In one example, UEGO sensor 200 is an embodiment of UEGO sensor 126 of FIG. 1. It will be appreciated, however, that the sensor of FIG. 2 may alternatively represent an intake oxygen sensor, such as sensor 172 of FIG. 1.

Sensor 200 comprises a plurality of layers of one or more ceramic materials arranged in a stacked configuration. In the embodiment of FIG. 2, five ceramic layers (elements) are depicted as layers 201, 202, 203, 204, and 205. These layers include one or more layers of a solid electrolyte capable of conducting ionic oxygen. Further, in some embodiments such as that shown in FIG. 2, a heater 207 may be disposed in thermal communication with the layers to increase the ionic conductivity of the layers. While the depicted UEGO sensor 200 is formed from five ceramic layers, it will be appreciated that the UEGO sensor may include other suitable numbers of ceramic layers.

Examples of suitable solid electrolytes include, zirconium oxide (also known as Zirconia $ZrO_2$) based materials. $ZrO_2$ is typically white in color. With usage, over time, the two Oxygen atoms may get removed from $ZrO_2$, changing white $ZrO_2$ to dark colored metallic Zirconium (Zr) causing blackening of the corresponding element. Primary causes for blackening to occur may include, but are not limited to, high voltage (in the over-potential region), variable voltage conditions, low air and oxygen conditions. The newly formed Zr not only has ionic conductivity but also is capable of electronic conductivity. The electronic conductivity may increase proportional to the extent of blackening.

The layer 202 includes a porous material or materials creating a diffusion path 210. The diffusion path 210 is configured to introduce exhaust gases into a first internal cavity (also termed as gas detecting cavity) 222 via diffusion. The diffusion path 210 may be configured to allow one or more components of exhaust gases, including but not limited to a desired analyte (e.g., $O_2$), to diffuse into the internal cavity 222 at a more limiting rate than the analyte can be pumped in or out by pumping electrodes pair 212 and 214. In this manner, a stoichiometric level of $O_2$ may be obtained in the first internal cavity 222.

The sensor 200 further includes a second internal cavity 224 within the layer 204 separated from the first internal cavity 222 by the layer 203. The second internal cavity 224 is configured to maintain a constant oxygen partial pressure equivalent to a stoichiometric condition, e.g., an oxygen level present in the second internal cavity 224 is equal to that which the exhaust gas would have if the air-fuel ratio was stoichiometric. The oxygen concentration in the second internal cavity 224 is held constant by pumping voltage $V_{cp}$. Herein, the second internal cavity 224 may be referred to as a reference cell.

A pair of sensing electrodes 216 and 218 is disposed in communication with first internal cavity 222 and the reference cell 224. The sensing electrodes pair 216 and 218 detects a concentration gradient that may develop between the first internal cavity 222 and the reference cell 224 due to an oxygen concentration in the exhaust gas that is higher than or lower than the stoichiometric level. A high oxygen concentration may be caused by a lean intake air or exhaust gas mixture, while a low oxygen concentration may be caused by a rich mixture.

The pair of pumping electrodes 212 and 214 is disposed in communication with the internal cavity 222, and is configured to electrochemically pump a selected gas constituent (e.g., $O_2$) from the internal cavity 222 through the layer 201 and out of the sensor 200. Alternatively, the pair of pumping electrodes 212 and 214 may be configured to electrochemically pump a selected gas through the layer 201 and into the internal cavity 222. Herein, the electrolytic layer 201 together with the pumping electrodes pair 212 and 214 may be referred to as an $O_2$ pumping cell. Also, the electrolytic layer 203 together with the electrodes pair 216 and 218 may be referred to as a Nernst cell (also known as a sensing cell). The electrodes 212, 214, 216, and 218 may be made of various suitable materials. In some embodiments, the electrodes 212, 214, 216, and 218 may be at least partially made of a material that catalyzes the dissociation of molecular oxygen. Examples of such materials include, but are not limited to, electrodes containing platinum and/or gold.

The sensing cell (Nernst cell) may passively measure the oxygen concentration in the first internal (gas detection) cavity 222. The pumping cell may adjust the oxygen concentration in the cavity 222 based on feedback from the sensing cell. An external comparator circuit may compare the voltage generated by the sensing cell to a reference voltage $V_p$. In one example, under normal operating conditions, the reference voltage $V_p$ may be 450 mV. The voltage generated across a Nernst cell with one electrode exposed to air (with ~20% oxygen concentration) and the other electrode exposed to a low oxygen concentration (~10 ppm oxygen) may be around 450 mV. This oxygen concentration (~10 ppm) may correspond to stoichiometry. If the oxygen concentration in the cavity 222 is less than the oxygen concentration corresponding to stoichiometry (~10 ppm) due to reductants such as carbon monoxide or hydrogen, the comparator circuit may send a signal to the pumping cell to pump oxygen into the cavity 222 from the exhaust. The oxygen will react with the reductants thus raising the oxygen concentration level until the level reaches the oxygen concentration corresponding to stoichiometry (~10 ppm) as measured by the sensing (Nernst) cell. The amount of all of these reductants in the cavity determines how much oxygen needs to be pumped into the cavity by the pumping cell to completely react. The pumping current $I_p$ is directly proportional to the oxygen concentration in the pumping cell. The amount oxygen pumped is just enough to completely react with all the reductants. The sensor may employ different techniques to determine the concentration of reductants. In one example, the pumping current which is proportional to the oxygen concentration in the pumping cell may be used to estimate the reductant concentration.

If the oxygen concentration in the cavity is greater than the oxygen concentration corresponding to stoichiometry (~10 ppm), a reverse method may take place. The sensing cell may measure a voltage less than the reference voltage $V_p$ (450 mV) and the comparator circuit may send a signal to the pumping cell to pump oxygen out of the cavity by applying a pumping current $I_p$ in the opposite direction. The pumping current $I_p$ is directly proportional to the amount of oxygen that is pumped out of the cell, which is in turn is directly proportional to the amount of oxygen diffusing into the cavity 222. This amount of oxygen may be directly proportional to the concentration of oxygen in the exhaust gas.

As described previously, with usage, blackening may occur in one or more electrolytes. As such, blackening may be different from thermal aging. As the pump cell experiences higher voltages during operation, it is more susceptible to blackening. In one example, metallic Zr may accumulate on the electrode 214 of the pump cell. The impedance of the sensor element can be estimated by measuring the voltage drop across the sensor element, for example by using an AC voltage based technique. A frequency scan (impedance spectroscopy) may be carried out with a same voltage (alternating) at a regular interval of time and the corresponding change in impedance may be monitored and analyzed using a frequency response analyzer (FRA). Different physicochemical processes occurring within the cell influence electron and ion transport, gas and solid phase reactant transport, heterogeneous reactions, etc. Such processes may have different characteristic time-constants and therefore are exhibited at different AC frequencies. When conducted over a broad range of frequencies, impedance spectroscopy can be used to identify and quantify the impedance associated with these various processes. For oxygen sensor 200, the impedance may be specifically measured across either the Nernst cell, or the pump cell, for example. Due to blackening (Zr accumulation), the electronic conductivity of the pump cell may increase, therefore a decrease in impedance of the pump cell may be detected. However, with usage and over time, grain boundary resistance of the pump cell may decrease due to thermal effects. This effect may be termed as thermal aging or de-graining effect. Nernst cell impedance may also decrease due to the same thermal effects. The inventors have recognized that a decrease in impedance due to thermal aging may not continue after the pump cell de-grains. Once the thermal aging stabilizes, on further application of AC voltage, no further change in each of pump cell and Nernst cell impedance may be observed due to thermal aging effects. Stabilization of thermal aging effect may occur sooner in a Nernst cell compared to the pump cell due to its distal positioning in relation to the heater.

Once it is confirmed that the thermal aging process has stabilized, it is possible to detect any Zr accumulation present on the electrode 214 of the pump cell. An AC voltage may be applied to each of the pump cell and Nernst cell and the corresponding voltage drop across the sensor element may be measured to estimate the change in impedance. If it is observed that on application of the higher voltage, there is a further drop in impedance in the pump cell, it may be inferred that blackening due to Zr accumulation has occurred on the electrode 214. On the other hand, blackening does not occur in the Nernst cell. Therefore on application of the higher voltage, no change in impedance should be observed at the Nernst cell when compared to a last measured impedance (estimated during the stabilization of thermal aging effects). Once the thermal aging effect stabilizes, there is no change observed in the Nernst cell impedance. Therefore, a change in impedance in the pump cell that occurs while there is no change in impedance in the Nernst cell may be correlated with the blackening of the UEGO sensor.

It should be appreciated that the oxygen sensor described herein is merely an example embodiment of a UEGO sensor, and that other embodiments of intake or exhaust oxygen sensors may have additional and/or alternative features and/or designs.

FIGS. 1 and 2 show example configurations of the oxygen sensor with relative positioning of the various components. The oxygen sensor depicted therein is one of an intake oxygen sensor coupled downstream of an intake throttle and an exhaust oxygen sensor coupled upstream of an emission control device. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example.

Figure 3:
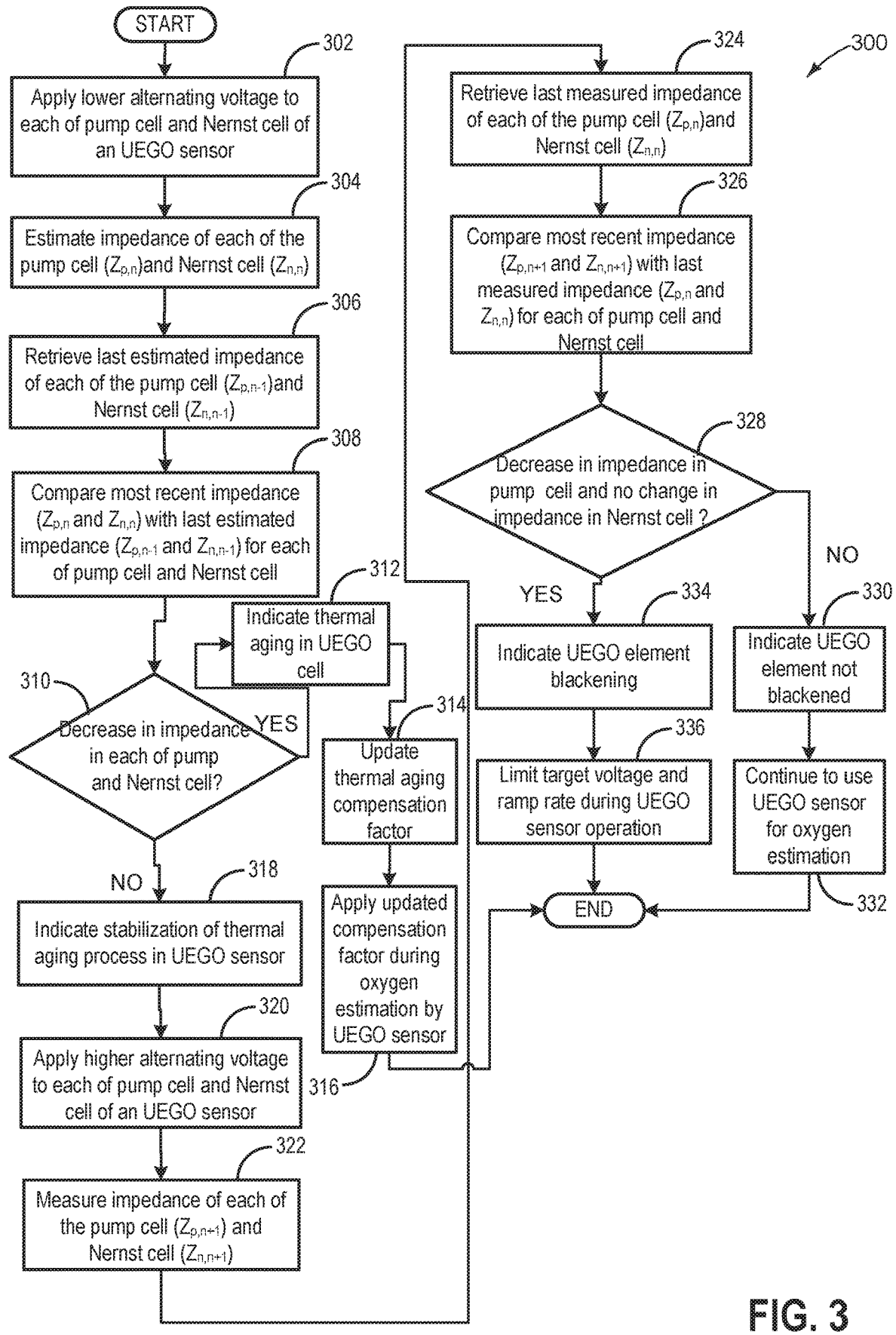
FIG. 3 shows a flow chart illustrating a method that can be implemented to detect thermal aging and element blackening in an oxygen sensor.

FIG. 3 illustrates an example method 300 for detecting thermal aging and element blackening in an UEGO (oxygen) sensor based on application of AC voltage and estimation of impedance. Instructions for carrying out method 300 and the rest of the methods included herein may be executed by a controller based on instructions stored on a memory of the controller and in conjunction with signals received from sensors of the engine system, such as the sensors described above with reference to FIGS. 1 and 2. The controller may employ engine actuators of the engine system to adjust engine operation, according to the methods described below.

At 302, a low value (peak) of AC voltage may be applied to each of a pump cell and Nernst cell of the UEGO (oxygen) sensor. The AC voltage application may take place opportunistically and/or periodically between regular oxygen estimation operations. The periodicity of AC voltage application may be based on one or more of timing in drive cycle, number of times variable reference voltage application carried out, threshold distance and/or threshold time of travel since last measurement. The pump cell may comprise of a pair of pumping electrodes and an electrolytic layer (such as electrolytic layer 201 together with pumping electrodes pair 212 and 214 in FIG. 2). Further, the Nernst cell may comprise of a pair of electrodes and an electrolytic layer (such as electrolytic layer 203 together with electrodes 216 and 218). An example of AC voltage applied to the sensor is shown in equation 1.

$$V(t)=V_{peak} \cdot \sin(\omega t) \quad (1)$$

Where, V(t) is the AC voltage, $V_{peak}$ is the peak voltage, $\omega$ is the frequency and t is time. A first and second frequency scan may be carried out in each of the pump and Nernst cell respectively. Each of the first and second frequency scans may be carried out by keeping the $V_{peak}$ constant, while gradually changing a frequency of the alternating current and monitoring the corresponding alternating currents. In one example, the frequency range used may be between $5 \times 10^6$ Hz and 1 Hz.

From the applied AC voltage and the measured alternating currents, at 304, an end point impedance of each of the pump ($Z_{p,n}$) and the Nernst cell ($Z_{n,n}$) may be estimated for the first and second frequency scans. The impedance of both the cells may have a real and an imaginary component. Pump cell and Nernst cell impedance may vary based on factors, such as the grain boundaries and the platinum electrodes of the respective cells. The Pump cell and Nernst cell may have different geometries and thicknesses therefore having different impedances. A part of the impedance relating to the cabling of the pump cell may be ignored during analysis. Pump cell and Nernst cell impedance will be further discussed with regard to FIGS. 4 and 5.

At 306, the routine includes retrieving the end point impedance values estimated from the previous frequency scans. The peak voltage and frequency range as employed in the current estimation may be the same as that used during the previous estimation. The end point impedances of the pump cell and Nernst cell impedance frequency scans ($Z_{p,n-1}$ and $Z_{n,n-1}$ respectively) may be retrieved from the memory of the controller. Between the current and the previous frequency scan, the UEGO sensor may have been used for oxygen estimation. Due to the application of variable voltages and high temperature during oxygen estimation, there may be thermal aging (also termed as de-graining effect) in each of the pump and Nernst cells. The primary reason for thermal aging in the cells is heating. The pump cell may experience a greater degree of thermal aging compared to the Nernst cell due its proximity to the heating elements. Alternatively, depending on the characteristics of the cell, the Nernst cell may experience a greater degree of thermal aging compared to the Nernst cell. In addition element blackening may occur in the pump cell due to the exposure to high voltages. Blackening may occur due to change in the material Zirconia ($ZrO_2$) that is present in the electrodes of the pump cell into Zirconium (Zr). A dark accumulation of metallic Zr may be observed on a pump cell electrode which may be termed as blackening. The thermal aging and blackening effects may further deteriorate over time and usage.

At 308, the controller may compare the current impedance value for the pump cell ($Z_{p,n}$, as determined at 304) and the Nernst cell ($Z_{n,n}$, as determined at 304) to the previously estimated corresponding impedance values for the pump cell ($Z_{p,n-1}$, as retrieved at 306) and the Nernst cell ($Z_{n,n-1}$, as retrieved at 306). Differentiating between thermal aging and blackening may be based on a monitored change in impedance of each of the pump cell and the Nernst cell following current application of the voltage relative to the monitored change in impedance of each of the pump cell and the Nernst cell following the immediately previous application of the voltage (with no frequency scans in between). For the pump cell, the difference between $Z_{p,n}$ and $Z_{p,n-1}$ may be estimated. Similarly for the Nernst cell, the difference between $Z_{n,n}$ and $Z_{n,n-1}$ may be estimated. At 310, the routine determines if there is decrease in impedance in each of pump and Nernst cell. If the difference in impedances (as determined at 308) between current and previous measurement for each of the Pump and Nernst cell impedances is negative, it may be inferred that there is a decrease in impedance in each of the pump and Nernst cell. In one example, if the difference in impedances (as determined at 308) between current and previous measurements for each of the pump and Nernst cell is higher than a threshold value of impedance, presence of thermal aging may be indicated. The threshold value of impedance may be either a constant value or may be dependent on (e.g., a function of) the impedance value estimated at the immediately previous frequency scan. In another example, indication of thermal aging may be based on end point impedance of each of the first and second frequency scans being lower than a first and second threshold impedance, respectively. The first and second threshold impedance may be based on the end point of each of the first and second frequency scan following a previous application of the voltage to each of the pump cell and the Nernst cell.

If at 310, it is determined that there is a decrease in impedance in each of the pump and the Nernst cell, at 312, it may be inferred and indicated that there is thermal aging effects present in each of the pump cell and the Nernst cell. The thermal aging effect (extent of aging) may be different in each of the pump and Nernst cells. The value of the difference between $Z_{p,n}$ and $Z_{p,n-1}$ and $Z_{n,n}$ and $Z_{n,n-1}$ may give an estimate of the extent of thermal aging in the pump cell and Nernst cell respectively. The extent of thermal aging may be indicated to the user by setting a diagnostic code or flag.

Based on detection of thermal aging effects in each of the pump and the Nernst cell, at 314, a thermal aging compensation factor for the UEGO sensor may be updated. The compensation factor would account for any inaccuracies arising in oxygen estimations with the sensor due to thermal aging effects. With the advancement of thermal aging, the compensation factor may be adjusted (increased) to ensure accurate oxygen estimations. At 316, the updated compensation factor may be utilized during further oxygen estimation by the UEGO sensor. In this way even with the presence of thermal aging effects, oxygen estimation may be performed accurately by the UEGO sensor.

If at 310, it is determined that there is no decrease in impedance in each of the pump and the Nernst cell, at 318, it may be inferred that the thermal aging (de-graining) process has stabilized. With usage over a period of time, each of the pump cell and the Nernst cell may de-grain and thereby the thermal aging may stabilize. Impedances from the pump cell and the Nernst cell may stabilize at different rates due to difference in thermal aging as experienced by each of the two cells. In one example, thermal aging in the Nernst cell may stabilize before that of the pump cell due to their difference in spatial distance from the heating element. Once the thermal aging effect has stabilized, the compensation factor used by the UEGO sensor for oxygen estimation may be held constant during future operations of the UEGO sensor.

At 320, the routine includes application of a of AC voltage to each of the pump cell and the Nernst cell of the UEGO sensor. The peak value of AC voltage applied at this stage may be equal to or higher compared to the peak value of AC voltage applied to the cells at 302. A frequency scan may be carried out in each of the two cells, keeping the $V_{peak}$ constant and the corresponding alternating currents may be monitored. In one example, the frequency range used may be between $5\times10^6$ Hz and 1 Hz. From the applied AC voltage and the measured alternating currents at 322, the impedance (end point of the frequency scan) of each of the pump ($Z_{p,n+1}$) and the Nernst cell ($Z_{n,n+1}$) may be estimated. As before, the impedance of both the cells may have a real and an imaginary component. At 324, the routine includes retrieving the impedance values estimated from the previous frequency scan. The previous frequency scan may have indicated the stabilization of thermal aging in each of the two cells. The Pump cell and Nerst cell impedances ($Z_{p,n}$ and $Z_{n,n}$ respectively) may be retrieved from the memory of the controller. Between the current and the previous frequency scan, the UEGO sensor may have been used for oxygen estimation causing further degradation due to blackening.

At 326, the controller may compare the current impedance value for the pump cell ($Z_{p,n+1}$, as determined at 322) and the Nernst cell ($Z_{n,n+1}$, as determined at 322) to the previously estimated corresponding impedance values for the pump cell ($Z_{p,n}$, as determined at 304) and the Nernst cell ($Z_{n,n}$, as determined at 304). For the pump cell, the difference between $Z_{p,n+1}$ and $Z_{p,n}$ may be estimated. Similarly for the Nernst cell, the difference between $Z_{n,n+1}$ and $Z_{n,n}$ may be estimated. At 328, the routine determines if there is a higher than threshold decrease in pump cell impedance while there is a lower than threshold decrease in Nernst cell impedance (e.g., Nernst cell impedance may remain substantially constant). The pump cell is more prone to be affected by the high reference voltage applied to it during oxygen estimation compared to the Nernst cell. Consequently, blackening is more likely to take place in the pump cell. Due to pump cell blackening, a pronounced decrease in pump cell impedance may be observed with the application of AC voltage whereas there may not be any variation in Nernst cell voltage with the application of equal voltage. In one example, if the difference in impedances (as determined at 326) between current and previous measurements for the pump cell is higher than a threshold and that for the Nernst cell is lower than a threshold value of impedance, presence of blackening in the pump cell may be indicated. The threshold value of impedance of each of the pump and the Nernst cell may be either a constant value or may be dependent on the impedance value as estimated from the previous frequency scans for each of the two cells. The magnitude of the decrease in pump cell impedance (shift in end point of frequency scan) may indicate the extent of blackening that may have occurred in the pump cell.

If a significant difference in pump cell impedance is not observed, at 330, the controller may indicate that the UEGO element may not have been affected by blackening. In that case, the functionality of the UEGO sensor may not be compromised due to blackening. At this time the thermal aging effects may also have been stabilized. Based on the indication that the UEGO element has not blackened, at 332, the sensor may continue to estimate oxygen and operate normally.

If at 328, it is determined that there is significant decrease in pump cell impedance and no change in the corresponding Nernst cell impedance, at 334, it may be inferred and indicated that the UEGO element has blackened. In response to detection of blackening, a flag or a diagnostic code may be set. Due to the repeated application of high voltage and the presence of high temperatures, $ZrO_2$ may have converted to Zr causing accumulation of the dark metallic Zr element on a pump cell electrode. Blackening is a form of UEGO sensor degradation and may affect the oxygen estimation capabilities of the sensor. Further a malfunction indicator lamp may be activated in order to notify the vehicle operator that the UEGO sensor is degraded and may require replacement.

In response to the detection of UEGO element blackening, at 336, the controller may limit (lower) the target voltage and ramp rates of reference voltages used in future sensor operations. By limited such conditions that cause blackening, further damage to the pump cell may be averted. Also, a compensation factor may be used during oxygen estimation, taking into account both thermal aging and blackening effects.

In this way, UEGO sensor degradation due to blackening may be detected using AC voltage and estimating corresponding impedances of each of the pump and the Nernst cell. Also using this method it is possible to differentiate between thermal aging effects and pump cell blackening.

FIG. 4 shows an example plot 400 of variation in pump cell impedance in a UEGO sensor with the application of AC voltages for a plurality of frequency scans. A controller may detect blackening in the UEGO sensor by monitoring changes in the impedance of the pump cell. An alternating current (AC) voltage may be applied to the pump cell of the UEGO sensor when the sensor is in a new condition and has not been used for oxygen estimation (for example, immediately after installation). The corresponding current may be recorded and the impedance may be estimated from the applied AC voltage and the measured current. This measurement may be carried out at the manufacturing facility. A frequency scan may be carried out by keeping the voltage and time constant and by varying the frequency of oscillation of the AC voltage. For every frequency value, the current may be measured and the impedance may be estimated. The impedance may have a real and an imaginary part. In this example the x-axis denotes the real part of the impedance (Z1) and the y-axis denotes the imaginary part of the impedance (Z2).

The impedance estimate from the first frequency scan, carried out on the pump cell of the new UEGO sensor is shown by the plot 402. The impedance plot may be divided into three sections S1, S2 and S3 based on the part of the pump cell that contributes to the impedance. The first section, S1, may correspond to the inductance due to cabling of the pump cell and thereby this part of the plot may not be taken into consideration during analysis and pump cell blackening detection. The second section, S2, may correspond to impedance arising due to the grain boundaries of the pump cell. Thermal aging in the pump cell is associated with the de-graining effect, thereby this part of the plot may show changes due to thermal aging. Also, element blackening may be detected by monitoring change in grain boundary impedance. The third section, S3, may correspond to the impedance associated with the platinum electrodes (such as electrodes 212 and 212 as shown in FIG. 2) of the pump cell. The impedance in this section may not change appreciably due to thermal aging and/or blackening effects. The end point of plot 402 (maximum value of real impedance) may be denoted by R1.

Once the UEGO sensor starts operating and estimating oxygen, the process of AC voltage application may be repeated periodically and/or opportunistically in order to detect thermal aging and/or blackening effects. In this example, ten minutes after UEGO sensor operation, AC voltage may be applied to the pump cell and the corresponding current may be measured. The corresponding impedance may be estimated and is shown in plot 404. The end point of plot 404 (maximum value of real impedance) may be denoted by R2. It may be observed from the plots 402 and 404, that the second section of plot 404 is smaller compared to the second section of plot 402. Also from the position of points R1 and R2 we observe a shift in the maximum value of real impedance. Thereby it may be inferred that there is a reduction in grain boundary impedance due to thermal aging effects after ten minutes of use.

Thereafter, a plurality of frequency scans may be carried out periodically and a corresponding impedance estimate may be recorded for detection of thermal aging and sensor degradation due to blackening. In this example, frequency scans were carried out after fifteen minutes, twenty minutes, twenty five minutes, thirty minutes, forty five minutes and one hour from the start of operation of the UEGO sensor. The corresponding impedance estimates are recorded. Plots 406 and 408 show impedance estimated for frequency scans carried out after 30 minutes and one hour from the start respectively. It may be observed that in each of the plots the impedance of the grain boundary region decreases. The consistent decrease in impedance may be attributed to thermal aging effects occurring in the pump cell of the UEGO sensor.

The plots from the other frequency scans as stated before are not included in the figure in order to maintain clarity. Impedance estimates that are not shown in the figure follow the trend of reduction in grain boundary impedance with usage and over time. The AC voltage applied each time to the pump cell may be of same magnitude (same peak and rms voltage). The effect of thermal aging on oxygen estimation by the UEGO sensor may be regulated by using a compensation factor. The compensation factor may account for any inaccuracies arising in oxygen estimations with the sensor due to thermal aging effects.

The vehicle controller may continue the process of periodically applying AC voltage, carrying out a frequency scan, measuring AC and estimating impedances until there is no further change observed in the grain boundary impedance. In this example, plot 410 shows a frequency scan carried out seventeen hours after the start of the sensor. The end point of plot 410 (maximum value of real impedance) may be denoted by R3. On comparing plot 410 with previous frequency scan plots (402, 404, 406, and 408) it may be observed that there is consistent decrease in grain boundary impedance with usage and over time. The maximum real impedance value R3 is lower compared to previous values (R1 and R2) of maximum real impedance recorded during previous frequency scans. This continued decrease in impedance may be due to thermal aging taking place in the pump cell. Thereby it may be inferred that reduction in grain boundary impedance may have continued due to thermal aging effects after seventeen hours of use.

In this example, a frequency scan is carried out after eighteen hours from the start of UEGO sensor operation, using the same value of peak AC voltage as used during the previously mentioned frequency scans. The corresponding impedance may be calculated from the AC measured after application of the voltage and shown in plot 412. It may be observed that there no appreciable change observed in impedance after the last frequency scan. Also the maximum value of real impedance (end point of the plot 412) may coincide with the maximum value of real impedance (R3) as estimated for the previous measurement (plot 410) carried out seventeen hours after the start of UEGO sensor operation. From the consistency in grain boundary impedance as observed from consecutive plots, it may be inferred that de-graining from repeated heating may have taken place in the pump cell. As a consequence of the de-graining effect, no further change in impedance is observed due to thermal aging effects. At this point it may be ascertained that the change in impedance due to thermal aging effects has stabilized and if any further change in impedance is observed (on application of voltage), the cause may be attributed to other factors such as presence of blackening in the pump cell.

Following the stabilization of the thermal aging process, in order to detect the presence of blackening, the controller may apply an AC voltage with a higher peak voltage value to the pump cell and carry out a frequency scan. The corresponding AC is measured and the estimated impedance is shown in plot 414. The maximum value of impedance (end point of the plot 410) may be denoted by R3. A marked decrease in grain boundary impedance may be observed from plot 414 when compared to previous impedance estimation plot 412. There is also a significant reduction in maximum real impedance value as observed from the shift in R4 compared to R3. From this significant decrease in grain boundary and the maximum value of impedance it may be inferred that blackening may have occurred in the pump cell. The extent of blackening i.e. the amount of dark metallic Zr accumulated on a pump cell electrode may be estimated from the degree of change in end point impedance of the frequency scan. In this example, the difference in impedance between end point impedances R4 and R3 may be used as a quantitative estimate for blackening. In response to the detection of UEGO element blackening, the controller may limit the target voltage and ramp rates for reference voltages used in future sensor operations. By limiting such conditions that cause blackening, further damage to the pump cell may be averted. In addition, on detection of UEGO element blackening, a diagnostic code and/or a flag may be set. In this way, by monitoring change in impedance in a pump cell, it is possible to differentiate and detect each of thermal aging and blackening effects in a UEGO sensor pump cell.

FIG. 5 shows an example plot 500 of variation in Nernst cell impedance in a UEGO sensor with the application of AC voltages for a plurality of frequency scans. It is possible to detect thermal aging in the UEGO sensor by monitoring change in impedance in the Nernst cell. An alternating current (AC) voltage may be applied to the Nernst cell of the UEGO sensor when the sensor is in new condition and has not been used for oxygen estimation. The corresponding current may be recorded and the impedance may be estimated from the applied AC voltage and measured AC. This measurement may be carried out at the manufacturing facility. A frequency scan may be carried out by keeping the voltage and time constant and varying the frequency of oscillation of the AC voltage. For every frequency value, the current may be measured and the impedance may be estimated. The impedance may have a real and an imaginary part. In this example the x-axis denotes the real part of the impedance (Z1) and the y-axis denotes the imaginary part of the impedance (Z2).

The impedance estimated from the first frequency scan carried out in the Nernst cell of a new UEGO sensor is shown by the plot 502. The end point impedance of plot 502 (maximum value of real impedance) may be denoted by I1. Once the UEGO sensor starts operating and estimating oxygen, the process of AC voltage application may be repeated periodically and/or opportunistically in order to detect thermal aging and/or blackening effects. In this example, again ten minutes after UEGO sensor operation, AC voltage may be applied to the Nernst cell and the corresponding current may be measured. The corresponding impedance may be estimated and is shown in plot 504. The end point impedance of plot 504 (maximum value of real impedance) may be denoted by I2. It may be observed from the plots 402 and 404, especially from the position of points I1 and I2 there is a shift in the maximum value of real impedance. Thereby it may be inferred that there is a reduction in Nernst cell impedance due to thermal aging effects after ten minutes of use.

Thereafter, a plurality of frequency scans may be carried out periodically and a corresponding impedance estimate may be recorded for detection of thermal aging. In this example, frequency scans were carried out after fifteen minutes, twenty minutes, twenty five minutes, thirty minutes, forty five minutes and one hour from the start of operation of the UEGO sensor. The corresponding impedance estimates were recorded. Plots 506 and 508 show impedance estimated for frequency scans carried out after 30 minutes and one hour from the start respectively. It may be observed that in each of the plots, the maximum value of impedance decreases. The consistent decrease in impedance may be attributed to thermal aging effects occurring in the Nernst cell of the UEGO sensor.

The plots from the other frequency scans are not included in the figure in order to maintain clarity. Impedance estimates that are not shown in the figure follow the trend of reduction in maximum impedance with usage and over time. The AC voltage applied each time to the Nernst cell may be of same magnitude (same peak and rms voltage). The effect of thermal aging on oxygen estimation by the UEGO sensor may be regulated by using a compensation factor. The compensation factor may account for any inaccuracies arising in oxygen estimations with the sensor due to thermal aging effects.

The controller in the vehicle may continue the process of applying AC voltage, carrying out a frequency scan, measuring AC and estimating impedances until no further change is observed in the maximum impedance of the Nernst cell. In this example, plot 510 shows a frequency scan carried out seventeen hours after the start of the sensor. The end point impedance of plot 510 (maximum value of real impedance) may be denoted by I3. On comparing plot 510 with previous frequency scan plots (502, 504, 506, and 508), it may be observed that there is consistent decrease in impedance with usage and over time. The maximum real impedance value I3 is lower compared to previously recorded values of maximum real impedances (I1 and I2). This decrease in impedance may be due to thermal aging taking place in the Nernst cell. Thereby it may be inferred that reduction in maximum value of impedance may continue due to thermal aging effects after seventeen hours of use. In one example, the decrease in maximum value of impedance as observed in the Nernst cell may be lower than the corresponding decrease in maximum value of impedance observed under same measurement conditions, for the pump cell (as seen in FIG. 4). This may be due to the variation in degrees of thermal aging as experienced by each of the two cells. The differences in thermal aging extents may arise due to different spatial distances of the two cells from the heating element.

In this example, a frequency scan is carried out after eighteen hours from the start of UEGO sensor operation using the same value of peak AC voltage as used during the previously mentioned frequency scans. The corresponding impedance may be calculated from the AC measured after application of the voltage and is shown in plot 512. It may be observed that there is no appreciable change observed in impedance after the last frequency scan. Also the maximum value of real impedance (end point of the plot 512) may coincide with the maximum value of real impedance (I3) as estimated for the previous measurement (plot 510) carried out seventeen hours after the start of UEGO sensor operation. From the consistency in decrease in impedance as observed from consecutive plots, it may be inferred that de-graining from repeated heating may have taken place in the Nernst cell. As a consequence of the de-graining effect, there is no further change in impedance observed due to thermal aging effects. At this point it may be ascertained that the change in impedance due to thermal aging effects has stabilized.

Following the stabilization of the thermal aging process, in order to confirm the presence of blackening in the pump cell of the same UEGO sensor, the controller may apply an AC voltage with a higher peak voltage value to the Nernst cell and carry out a frequency scan. During UEGO sensor operation, high reference voltage is not applied to the Nernst cell thereby the possibility of blackening of Nernst cell electrodes may be low. The corresponding AC is measured and the estimated impedance is shown in plot 514. It may be observed that there is no appreciable change in impedance when compared to that from the last two frequency scans (plots 512 and 510). Also the maximum value of real impedance (end point of the plot 514) may coincide with the maximum value of real impedance (l3) as estimated for the previous measurements (plot 512 and 510). In this way, if under same measuring conditions, a significant decrease in impedance is observed in the pump cell but no change in impedance is observed in the Nernst cell, occurrence of blackening in the pump cell may be confirmed.

FIG. 6 shows an example operating sequence 600 illustrating detection of thermal aging and blackening effects in a UEGO sensor based on change in pump and Nernst cell impedances. The horizontal axis (x-axis) denotes time and the vertical markers t1-t7 identify significant times in the detection process.

The first plot (line 602) denotes the peak alternating current (AC) voltage applied to each of the pump cell and the Nernst cell. The lower peak voltage value is indicated by V1 and the higher peak voltage value is indicated by V2. The corresponding impedance values may be estimated from the AC currents. The second plot (line 604) shows the maximum value of impedance as estimated in the pump cell of the UEGO sensor. Three significant values of pump cell impedances are shown by dotted lines Z_P1, Z_P2 and Z_P3 respectively. The third plot (line 606) shows the maximum value of impedance as estimated in the Nernst cell of the UEGO sensor. Two significant values of Nernst cell impedances are shown by dotted lines Z_N1 and Z_N2 respectively. In the fourth and final plot, lines 608 and 610 represent flags indicating thermal aging and blackening effects detected in the UEGO sensor.

Prior to time t1, an alternating current (AC) voltage of peak value V1 may be applied to each of the pump cell and the Nernst cell of the UEGO sensor. The corresponding currents may be recorded in each cell and the impedances may be estimated from the applied AC voltage and measured AC. This measurement may be carried out when the UEGO is new at the manufacturing facility. A frequency scan may be carried out by keeping the peak voltage and time constant and varying the frequency of oscillation of the AC voltage. The maximum values of impedances as estimated from the applied AC voltages and measured currents for each of the pump and the Nernst cell are seen from plots 604 and 606 respectively. The maximum impedance value for the pump cell and the Nernst cell are shown by dotted lines Z_P1 and Z_N1 respectively. The impedance values (Z_P1 and Z_N1) for each of the two cells may be stored in the memory of the controller. The application of AC voltage and the corresponding impedance estimation may continue until time t1.

Between time t1 and t2, the controller in the vehicle may continue the process of applying AC voltage (of peak voltage value V1), carrying out a frequency scan, measuring AC and estimating impedances multiple times, under same conditions. Each time impedance of each of the two cells are estimated, the value may be compared to the impedance value from the previous measurement. Prior to time t2, neither one of thermal aging and blackening may be detected in the UEGO sensor, thereby the flag may be maintained in the OFF position.

Between time t2 and t3, an AC voltage (of peak value V1) may be applied to each of the pump cell and the Nernst cell and the corresponding maximum values of impedances may be estimated. During this time, the maximum impedance value for the pump cell and the Nernst cell are shown by dotted lines Z_P2 and Z_N2 respectively. On comparing the values of current pump cell and Nernst cell impedances (Z_P2 and Z_N2) to previously measured values such Z_P1 and Z_N1 respectively, a decrease in impedance may be observed for each of the two cells. The decrease in impedance may be attributed to thermal aging effects. Thermal aging may occur in each of the pump and Nernst cells due to continuous usage at high temperatures. Based on the detection of thermal aging effects in each of the pump and the Nernst cell, a flag or diagnostic code (line 608) may be set. Further, during oxygen estimation using the UEGO sensor, a compensating factor may be used to avoid any inaccuracies in estimation due to thermal aging effects.

Between time t3 and t4, the UEGO sensor is continued to be operated for oxygen estimation. The flag for the thermal aging effect may be maintained in the ON position and the compensation factor may be used during UEGO sensor operation.

Between time t4 and t5, an AC voltage (of peak value V1) may be applied to each of the pump cell and the Nernst cell and the corresponding maximum values of impedances may be estimated, as before. During this time, it may be observed that the maximum values of each of the pump cell and the Nernst cell impedances have remained unchanged at Z_P2 and Z_N2 respectively. Thereby at time t2 it may be inferred that thermal aging effects may have stabilized in the UEGO sensor. Thereafter, by application of voltage to each of the pump and the Nernst cell, any further change in impedance due to thermal aging effects may not be observed. Between time t5 and t6, the UEGO sensor is continued to be used for oxygen estimation. The flag indicating thermal aging may be continued to be maintained in the ON position and the compensation factor may be used during UEGO sensor operation.

After the stabilization of thermal aging process, between time t6 and t7, an AC voltage of peak value V2 may be applied to each of the pump cell and the Nernst cell. A frequency scan may be carried out keeping the peak voltage and time constant and by varying the frequency of the oscillation. The peak value V2 may be higher than the peak value (V1) of the voltage previously used during thermal aging detection. The higher voltage may be beneficial for better estimation of UEGO sensor blackening. Following the application of peak voltage V2, the corresponding current may be measured and the maximum impedance values for each of the pump and Nernst cell may be estimated. It may be observed at this time that the maximum value of pump cell impedance shows a significant decrease from Z_P2 to Z_P3. From this decrease in impedance it may be inferred that blackening may have occurred in the pump cell. However at this time, the Nernst cell impedance may remain constant at Z_N2. Since lower reference voltage is applied to the Nernst cell during operation of the UEGO sensor, the possibility of occurrence of blackening is low in the Nernst cell. Thereby, if under same measuring conditions, a significant decrease in impedance is observed in the pump cell but no change in impedance is observed in the Nernst cell, occurrence of blackening in the pump cell may be confirmed.

In response to the detection of UEGO element blackening, the flag or diagnostic code for blackening detection is set to ON position (line 610). In addition, the controller may limit the target voltage and voltage ramp rates used in future sensor operations. By limiting such conditions that cause blackening, further damage to the pump cell may be averted. The thermal aging flag (line 608) may also be maintained in the ON position. A compensation factor may be used during oxygen estimation, taking into account both thermal aging and blackening effects.

One example method for an engine comprises differentiating between thermal aging and blackening of an oxygen sensor element based on a monitored change in impedance of each of a pump cell and a Nernst cell of the oxygen sensor following application of a voltage. In the preceding example, additionally or optionally, the voltage is an alternating voltage. In any or all of the preceding examples, differentiating based on a monitored change additionally or optionally, includes differentiating based on the monitored change following a current application of the voltage relative to the monitored change in impedance of each of the pump cell and the Nernst cell following a previous application of the voltage. In any or all of the preceding examples, additionally or optionally, the differentiating includes indicating thermal aging in response to the monitored change in impedance of each of the pump cell and the Nernst cell being higher than a threshold value; and indicating blackening in response to the monitored change in impedance of the pump cell being higher than the threshold value while the monitored change in impedance of the Nernst cell being lower than the threshold value. In any or all of the preceding examples, additionally or optionally, the threshold value is one of a constant value and a value based on the impedance following the previous application of the voltage. In any or all of the preceding examples, additionally or optionally, indicating blackening further includes indicating a level of blackening based on change in impedance of pump cell following the previous application of voltage. Any or all of the preceding examples further comprises additionally or optionally, lowering one or more operating parameters of the oxygen sensor based on the indication of blackening, wherein the operating parameters include one or more of a reference voltage and a voltage ramp rate. Any or all of the preceding examples further comprises, additionally or optionally, in response to the indication of thermal aging, adjusting a compensation factor for oxygen estimation. In any or all of the preceding examples, additionally or optionally, the differentiating includes differentiating based on an end point impedance of a frequency scan generated following application of the voltage to the pump cell, and indicating blackening of the oxygen sensor based on the end point impedance being lower than a threshold impedance. In any or all of the preceding examples, additionally or optionally, the threshold impedance is based on the end point of the frequency scan following a previous application of the voltage to the pump cell.

Another example method comprises periodically applying an alternating voltage to each of a pump cell and a Nernst cell of an oxygen sensor; generating a frequency scan for each of the pump cell and the Nernst cell including a change in impedance upon the application of voltage; indicating blackening based on an end point of the frequency scan for each of the pump cell and the Nernst cell. In the preceding example, additionally or optionally, periodically applying voltage includes applying an alternating voltage once every drive cycle, after a threshold distance of travel, or after a threshold period of time elapsed since a previous application. In any or all of the preceding examples, additionally or optionally, the frequency scan includes applying the alternating voltage to each of the pump cell and the Nernst cell while keeping a peak voltage constant; gradually changing a frequency of the alternating voltage; measuring a pumping current following the application of the alternating voltage; and calculating the impedance of each of the pump cell and the Nernst cell based on the applied voltage and the measured pumping current. In any or all of the preceding examples, additionally or optionally, the frequency scan includes a first frequency scan of the pump cell following the application of the alternating voltage and a second frequency scan for the Nernst cell following the application of the alternating voltage. Any or all of the preceding examples further comprising, additionally or optionally, indicating thermal aging based on end point impedance of each of the first and second frequency scan being lower than a first and second threshold impedance, respectively, and indicating blackening based on end point impedance of the first frequency scan being lower than the first threshold impedance and the end point impedance of the second frequency scan being equal to the second threshold impedance. In any or all of the preceding examples, additionally or optionally, the first and second threshold impedance is based on the end point of each of the first and second frequency scan following a previous application of the voltage to each of the pump cell and the Nernst cell. Any or all of the preceding examples further comprises, additionally or optionally, in response to the indication of thermal aging, adjusting a compensation factor for oxygen estimation; and in response to the indication of blackening, lowering operating parameters including reference voltage and voltage ramp rate of the oxygen sensor.

In yet another example, a vehicle engine comprises an engine including an intake and an exhaust; an oxygen sensor coupled to the engine exhaust, the oxygen sensor including a pump cell and a Nernst cell; and a controller with computer readable instructions stored on non-transitory memory for: applying a voltage to each of the pump cell and the Nernst cell; learning the impedance profile of each of the pump cell and the Nernst cell; and in response to change in impedance profile between two successive applications of voltage of the pump cell indicating blackening in oxygen sensor. In the preceding example, additionally or optionally, the impedance profile of the pump cell includes each of a first, second and third section, wherein the first section is based on impedance of pump cell cabling, the second section is based on impedance of pump cell grain boundaries, and the third section is based on impedance of pump cell electrodes. In any or all of the preceding examples, additionally or optionally, indication of blackening is based on change in the impedance of the second section in the impedance profile following the second section of an impedance profile of previous measurement.

A further example method comprises in a first mode of operation of an oxygen sensor: flowing exhaust gas from a combustion engine into a first cavity formed on one side by a zirconium oxide layer and on another side by a ceramic layer, the ceramic layer positioned between the first cavity and a second cavity containing a reference gas; applying a first voltage across the zirconium oxide layer to pump oxygen ions between the first cavity and the exhaust gas;

applying a second voltage across the ceramic layer, limiting the first voltage when the second voltage reaches a threshold; and in a second mode of operation of the oxygen sensor, detecting breakdown of a portion of the zirconium oxide layer to zirconium by comparing a change in impedance of the zirconium layer to a change in impedance of the ceramic layer. In the preceding example, additionally or optionally, the ceramic layer is a first ceramic layer, and wherein the oxygen sensor further includes a pump cell and a Nernst cell, the pump cell comprising the first ceramic layer and a first electrode pair connected to a voltage source, the Nernst cell comprising a second ceramic layer and a second electrode pair connected to the voltage source, wherein each of the first and second electrode pair comprise Zirconium oxide layers. In any or all of the preceding examples, additionally or optionally, the second mode of operation includes periodically applying an alternating voltage to each of the pump cell and the Nernst cell, generating a frequency scan for each of the pump cell and the Nernst cell including a change in impedance upon the periodic application of voltage, and indicating breakdown of a portion of zirconium oxide to zirconium based on an end point of the frequency scan for each of the pump cell and the Nernst cell. Any or all of the preceding examples further comprises, additionally or optionally, in response to the indication of breakdown of the portion of the zirconium oxide to zirconium, lowering one or more of a reference voltage and a voltage ramp rate of the oxygen sensor.

In this way, by monitoring a change in impedance in each of the pump and the Nernst cell, thermal aging effects and element blackening may be detected in an oxygen (such as a UEGO) sensor. Using this method it is possible to differentiate between thermal ageing effects and oxygen sensor blackening. The technical effect of differentiating between thermal aging effects and element blackening in an oxygen sensor is that corresponding corrective measures may be employed for each effect. Thereby, it is possible to maintain the accuracy of oxygen estimation as the sensor ages by using appropriate corrective factors to compensate for thermal aging effects. Once element blackening is detected, further damage to the sensor due to blackening may be limited by taking preventive measures such as using a lower target voltage and a conservative ramp rate for application of reference voltages during oxygen estimations. By effectively detecting thermal aging and blackening in an oxygen sensor, accuracy and reliability of oxygen sensor operation is maintained without any effect on engine operations.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method comprising:
in a first mode of operation of an oxygen sensor: flowing exhaust gas from a combustion engine into a first cavity formed on one side by a zirconium oxide layer and on another side by a ceramic layer, the ceramic layer positioned between the first cavity and a second cavity containing a reference gas; applying a first voltage across the zirconium oxide layer to pump oxygen ions between the first cavity and the exhaust gas; and applying a second voltage across the ceramic layer, limiting the first voltage when the second voltage reaches a threshold; and
in a second mode of operation of the oxygen sensor, detecting breakdown of a portion of the zirconium oxide layer to zirconium by comparing a change in impedance of the zirconium oxide layer to a change in impedance of the ceramic layer.

2. The method of claim 1, wherein the ceramic layer is a first ceramic layer, and wherein the oxygen sensor further includes a pump cell and a Nernst cell, the pump cell comprising the first ceramic layer and a first electrode pair connected to a voltage source, the Nernst cell comprising a second ceramic layer and a second electrode pair connected to the voltage source, wherein each of the first and second electrode pairs comprises zirconium oxide layers.

3. The method of claim 2, wherein the second mode of operation includes periodically applying an alternating voltage to each of the pump cell and the Nernst cell, generating a frequency scan for each of the pump cell and the Nernst cell including a change in impedance upon the periodic application of voltage, and indicating the breakdown of the portion of the zirconium oxide layer to zirconium based on an end point of the frequency scan for each of the pump cell and the Nernst cell.

4. The method of claim 3, further comprising, in response to the indication of the breakdown of the portion of the zirconium oxide layer to zirconium, lowering one or more of a reference voltage and a voltage ramp rate of the oxygen sensor.

* * * * *